United States Patent [19]

McCoy

[11] Patent Number: 5,135,517

[45] Date of Patent: Aug. 4, 1992

[54] EXPANDABLE TUBE-POSITIONING APPARATUS

[75] Inventor: William C. McCoy, Zionsville, Ind.

[73] Assignee: Catheter Research, Inc., Indianapolis, Ind.

[21] Appl. No.: 554,352

[22] Filed: Jul. 19, 1990

[51] Int. Cl.$^5$ .......................................... A61M 25/00
[52] U.S. Cl. .................................. 604/281; 604/105; 606/198
[58] Field of Search ............... 604/96, 105, 107, 264, 604/280–281; 606/191, 194, 198; 128/4 SM; 623/1, 12

[56] References Cited

U.S. PATENT DOCUMENTS

| | | |
|---|---|---|
| 625,382 | 5/1899 | Clark . |
| 679,671 | 7/1901 | Hannigan . |
| 827,193 | 7/1906 | Thrash . |
| 1,621,159 | 3/1927 | Evans . |
| 2,586,553 | 2/1952 | Moscarello . |
| 3,490,457 | 1/1970 | Petersen . |
| 3,868,956 | 3/1975 | Alfidi et al. . |
| 3,968,800 | 7/1976 | Vilasi . |
| 4,168,709 | 9/1979 | Bentov . |
| 4,292,961 | 10/1981 | Kawashima . |
| 4,320,762 | 3/1982 | Bentov . |
| 4,427,000 | 1/1984 | Ueda . |
| 4,445,892 | 5/1984 | Hussein et al. . |
| 4,522,195 | 6/1985 | Schiff . |
| 4,543,090 | 9/1985 | McCoy . |
| 4,585,000 | 4/1986 | Hershenson . |
| 4,601,705 | 7/1986 | McCoy . |
| 4,692,139 | 9/1987 | Stiles . |
| 4,758,222 | 7/1988 | McCoy .................................. 604/95 |
| 4,777,799 | 10/1988 | McCoy et al. ........................ 60/528 |
| 4,781,682 | 11/1988 | Patel . |
| 4,790,624 | 12/1988 | Van Hoye et al. . |
| 4,791,913 | 12/1988 | Maloney . |
| 4,919,133 | 4/1990 | Chiang .............................. 606/159 |
| 5,025,799 | 6/1991 | Wilson .............................. 128/772 |
| 5,034,001 | 7/1991 | Garrison et al. ...................... 604/53 |

FOREIGN PATENT DOCUMENTS

| | | |
|---|---|---|
| 2805749 | 8/1978 | Fed. Rep. of Germany . |
| 3034453 | 3/1982 | Fed. Rep. of Germany . |
| 3532653 | 3/1987 | Fed. Rep. of Germany . |
| 955490 | 4/1964 | United Kingdom . |

Primary Examiner—C. Fred Rosenbaum
Assistant Examiner—C. Maglione
Attorney, Agent, or Firm—Barnes & Thornburg

[57] ABSTRACT

An apparatus is provided for positioning a core member within a passageway formed in a body. The apparatus includes at least one positioning element and a control mechanism for moving the positioning element relative to a core member. The positioning element includes a pair of end portions appended to the core member and a flexible central portion intermediate the end portions for movement relative to the core member. The positioning element is configured so that the flexible central portion moves in response to a stimulus from the control mechanism to assume a predetermined position engaging an interior wall of the body passageway and thus biasing the core member into a selected orientation within the passageway.

31 Claims, 4 Drawing Sheets

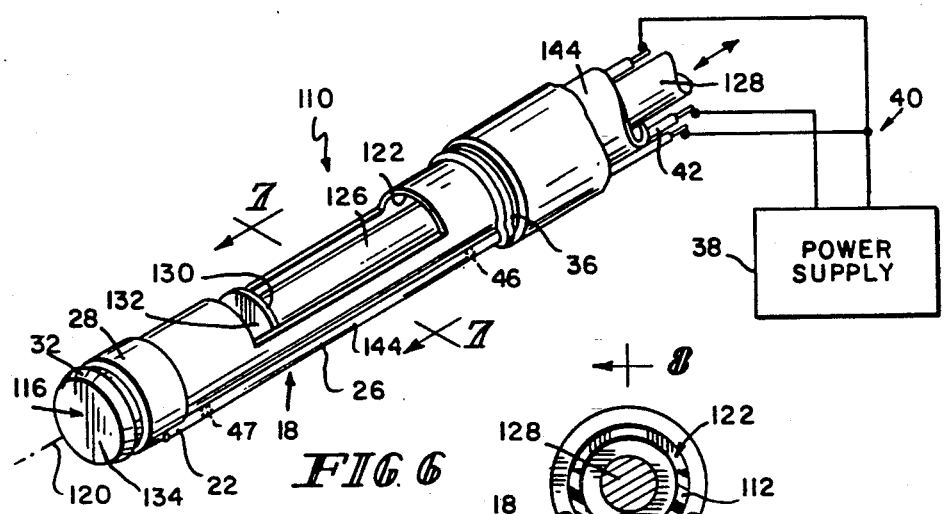
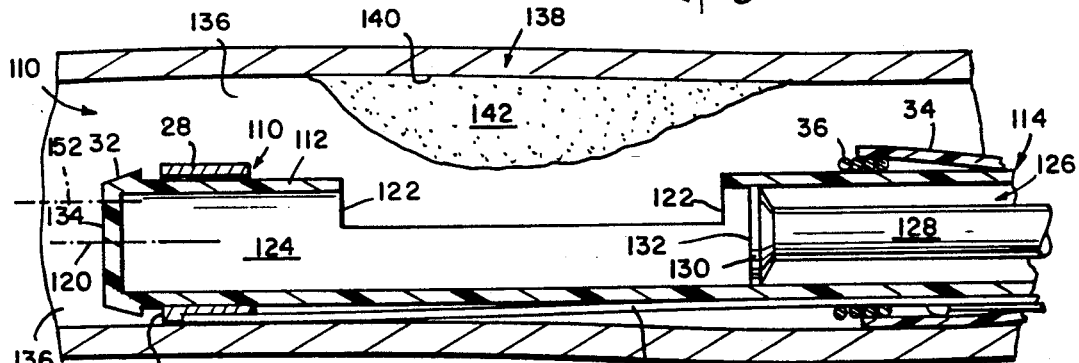
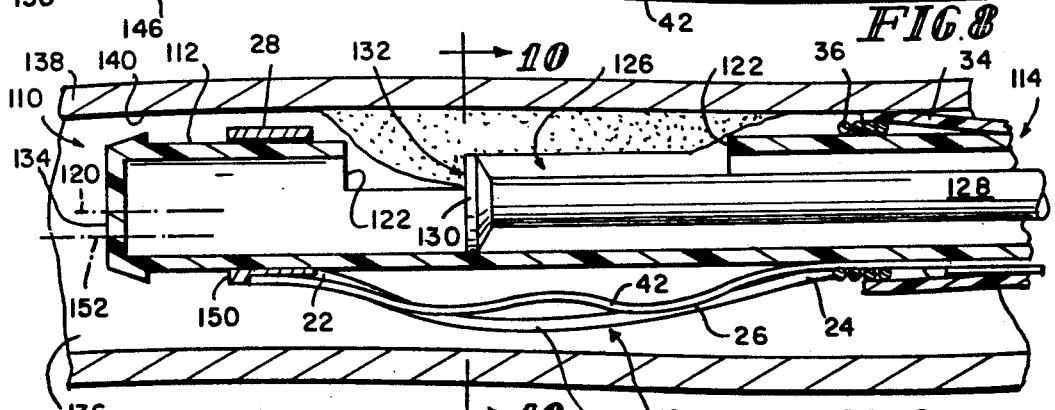
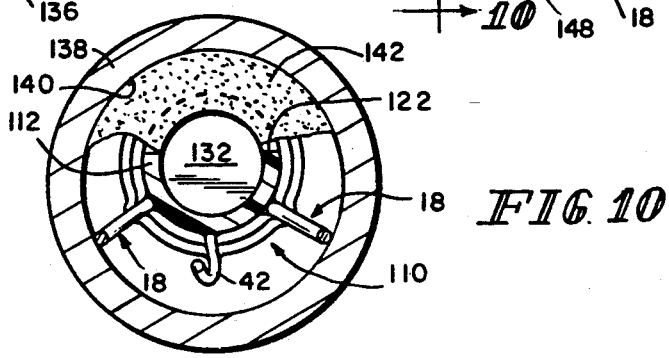

EXPANDABLE TUBE-POSITIONING APPARATUS

BACKGROUND AND SUMMARY OF THE INVENTION

The present invention relates to catheters, cannulae, and the like, and particularly to catheters that are steerable through body cavities and aimable at obstructions, organs, or tissue within the body from a position external to the body. More particularly, the present invention relates to a tube provided at the distal end of a catheter and apparatus that is operable to position or center the tube within a body cavity.

A great deal of research effort has focused on providing a catheter having a distal end which, when inserted into a body, is readily steerable and aimable to advance the catheter through body cavities and passageways. It has been observed that materials exhibiting mechanical memory properties triggered by heat are particularly useful for enhancing the maneuverability of catheters or like devices. The materials are commonly called "temperature-activated memory materials" or "shape memory alloys" because they move to assume a predetermined shape when heated to a predetermined temperature.

Nitinol, a nickel-titanium alloy, is one such temperature-activated memory material that has been formed into memory element strips and deployed in the distal end of a catheter. Heating the nitinol memory element strips to a given temperature using an electric current provided by a power supply causes the memory elements to deform to assume a predetermined shape, thereby deflecting the distal end of the catheter. See, for example, U.S. Pat. Nos. 4,543,090; 4,601,705; and 4,758,222 for descriptions of known memory element systems for steering and aiming catheters, cannulae, and the like.

While devices of the type described above enable an operator to steer a catheter by remote control to a particular destination within a body cavity, it is often necessary to position the catheter precisely in a certain location or orientation within the cavity once the destination is reached. For example, once a catheter has reached its destination, it might be desired to center the catheter within the cavity to aim a laser beam or the like emanating from the catheter precisely in a predetermined direction.

Alternatively, upon arrival of the catheter at its destination, certain applications might require the catheter to shift within the cavity to an off-center position close to an interior wall of the body cavity. Foreign matter, such as plaque, is known to accumulate on the interior walls of certain body cavities reachable by a steerable catheter. In such circumstances, foreign matter on the interior wall of a body cavity could be dislodged more easily using a catheter of enhanced maneuverability that could be shifted by remote control to an off-center position within the body cavity directly contacting the foreign matter.

One object of the present invention is to provide a readily steerable catheter, cannula, or the like which has a distal end that is easily maneuvered by remote control to occupy a predetermined position or orientation within a body cavity once the catheter has been steered through the body cavity to reach its destination.

Another object of the present invention is to provide an apparatus at the distal end of a catheter, cannula, or the like which is operable by remote control to move the distal end to a "centered" position along the central axis of the body cavity. In come cases, it also may be desirable to move the distal end to a predetermined off-center position within the body cavity.

Yet another object of the present invention is to provide a catheter, cannula, or the like having a distal end that includes scoop means for collecting plaque or other foreign matter accumulated on an interior wall of a body cavity and an apparatus that is operable by remote control to engage an interior wall of the body cavity and push the scoop means into a mound of plaque accumulated on another portion of the interior wall of the body cavity so that some of the plaque is deposited into a collection space formed in the catheter.

According to the present invention, an apparatus is provided for positioning a core member within a passageway formed in a body. The apparatus includes means for moving the core member relative to an internal wall defining the passageway. The moving means includes at least one temperature-activated memory element having spaced-apart attachment portions and a shape memory portion disposed therebetween. The spaced-apart attachment portions are coupled to the core member, while the shape memory portion is configured to move with respect to the core member when heated to a predetermined temperature.

The apparatus also includes control means for selectively heating the at least one memory element to the predetermined temperature. When so heated, the shape memory portion of the at least one memory element moves away from the core member to engage the internal wall of the passageway, thereby positioning the core member in a preselected orientation or position within the passageway. The control means is coupled to the attachment portions of the at least one memory element.

According to one aspect of the present invention, the apparatus includes several temperature-activated memory elements spaced equiangularly about the circumference of a tubular core member provided at the distal end of a catheter. When electrical current is supplied to heat the memory elements to a predetermined temperature, they expand outwardly away from the core member to engage the internal wall of the passageway containing the core member so as to center the core member along a central axis of the passageway. The core member will remain in its centered position as long as the memory elements are heated to their predetermined temperature.

According to another aspect of the present invention, the apparatus includes at least one temperature-activated memory element positioned on a tubular core member so that upon being heated to its predetermined transformation temperature, the memory element expands outwardly away from the core member to engage a particular portion of an interior wall of a passageway. The movement of the memory element away from the core member and against the wall portion moves the core member toward an opposite wall portion of the passageway. Thus, the core member is moved to a specified "off-center" position within the passageway.

In one embodiment, the tubular core member is formed to include a hollow interior cavity. Scraping means provided within the interior cavity is movable therein past a side opening formed in the core member. Advantageously, the core member can be moved by remote control using the inventive apparatus to the off-center position so that an accumulation of plaque or other foreign matter on an internal wall of the passageway is introduced into the hollow interior cavity through the side opening in the tubular core member. The scraping means is movable within the tubular core member to displace plaque admitted into hollow interior cavity and move it further into a collection space provided at one end of the cavity for storage. The catheter can then be removed from the patient and the plaque that was gathered and stored in the catheter can be removed from the catheter for analysis or disposal.

According to yet another aspect of the present invention, the apparatus includes a tubular core member having a heat-conductive tip affixed at its distal end and also includes means extending through tubular core member for conducting heat to the heat-conductive tip. For example, laser or fiber optics means could be employed to provide the heat-conducting means. The apparatus also includes at least one temperature-activated memory element having an end affixed to the heat-conductive tip. Advantageously, heat is conducted through the tubular core member to heat the heat-conductive tip. Heat from the tip is transferred to the temperature-activated memory element by conduction to heat the memory element to its transformation temperature. The temperature-activated memory element expands upon heating to engage an interior wall of a passageway to position the core member within the passageway.

According to still another aspect of the present invention, the apparatus includes at least one control element coupled to a tubular core member. In a preferred embodiment, the control element is a temperature-activated memory element. The control element has a flexible central portion lying between a pair of end portions. The apparatus also includes means for anchoring a first of the end portions to a proximal end of the core member. In addition, the apparatus includes collar means for slidably coupling a second of the end portions to a distal end of the core member. Advantageously, the flexible central portion can move away from the core member to engage an interior wall in a body passageway as the collar means attached to the second end portion slides on the distal end of the core member. This sliding movement can occur even though the first end portion is rigidly fixed to the proximal end of the core member.

According to yet another aspect of the present invention, the apparatus includes means for anchoring both first and second end portions of each of at least one control element to a core member. Again, each control element is desirably a temperature-activated memory element. A flexible central portion lying between the end portions of each control element is free to move relative to the core member to engage an interior wall in a body passageway without causing the end portions to move relative to the core member. Advantageously, the flexible central portion may be initially allowed to assume an undetermined configuration. It can then be moved (e.g. by heat in the case of a temperature-activated memory element) to assume a predetermined configuration acting against an interior wall in a body passageway to cause the core member to move to assume a predetermined location or orientation within the body passageway.

Additional objects, features, and advantages of the invention will become apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which:

FIG. 6 is a perspective view of another embodiment of an apparatus in accordance with the present invention using a slidable collar and showing a core member formed to include a storage cavity and a scraping blade for pushing matter into the storage cavity to collect plaque or other foreign matter deposited on an inner wall in the body passageway;

FIG. 7 is a transverse cross-sectional view taken along line 7—7 of FIG. 6 showing the relative location of two memory elements about the periphery of the core member of FIG. 6;

FIG. 8 is a longitudinal cross-sectional view taken along line 8—8 of FIG. 6 showing the apparatus inserted into a body passageway, and one of the memory elements attached to the core member in an initial, unexpanded configuration;

FIG. 9 is a view similar to that of FIG. 8 showing the memory element in its expanded configuration as it acts against an inner wall of the body passageway to bias the core member to an off-center position in the passageway;

FIG. 10 is a transverse cross-sectional view taken along line 10—10 of FIG. 9 showing the orientation of the two memory elements biasing the core member to an off-center position;

DETAILED DESCRIPTION OF THE DRAWINGS

Figure 1:
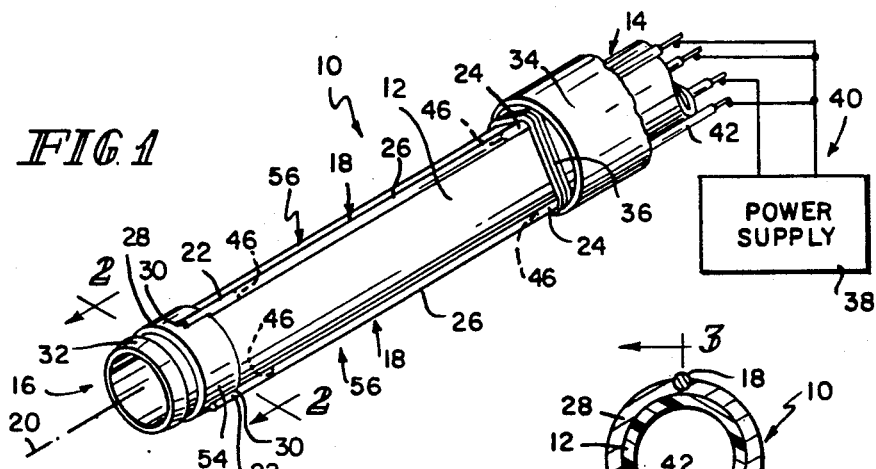
FIG. 1 is a perspective view of an apparatus in accordance with a first embodiment of the present invention mounted on a core member at the distal end of a catheter using a slidable collar at the distal end of the core member.

A positioning apparatus 10 shown in FIG. 1 includes a core member 12 having a base portion 14 and a distal end 16. Apparatus 10 also includes a plurality of temperature-activated memory elements 18 extending parallel to a longitudinal axis 20 of core member 12. Each memory element 18 has a distal attachment portion 22, a proximal attachment portion 24, and a shape memory portion 26. It will be appreciated that core member 12 could be a catheter, cannula, or other device configured to be maneuvered through body passages. Alternatively, the lumen of core member 12 could be sized to receive a catheter, cannula, or the like. Advantageously, the shape of memory elements 18 can be varied by remote control to change the position of core member 12 in a body passage.

At distal end 16 of core member 12, apparatus 10 includes a slip collar 28 mounted on core member 12 for reciprocable movement along longitudinal axis 20. Slip collar 28 is formed to include longitudinally extending grooves 30 for receiving distal attachment portions 22 of memory elements 18. A flange 32 formed at distal end 16 of core member 12 prevents slip collar 28 from disengaging core member 12 by sliding longitudinally beyond distal end 16.

Figure 3:
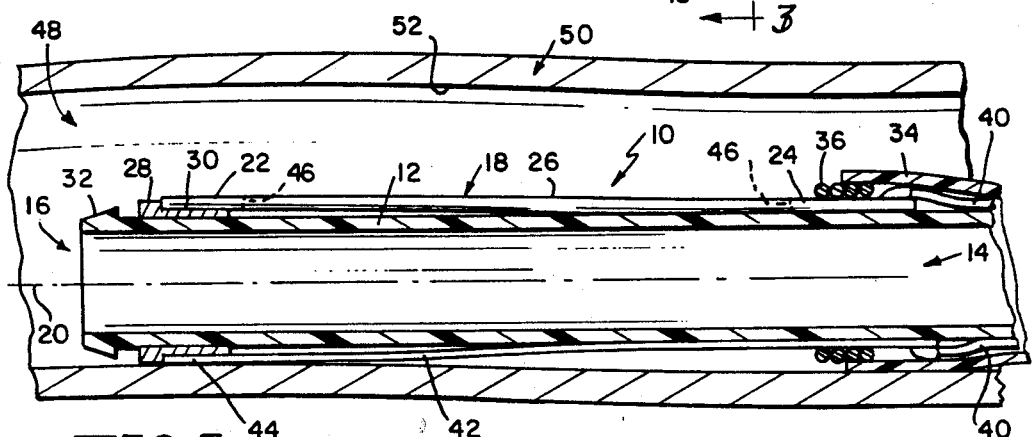
FIG. 3 is a longitudinal cross-sectional view taken along line 3—3 of FIG. 1 showing the apparatus inserted into a body passageway and two of the memory elements attached to the core member in an initial, unexpanded configuration.
Figure 4:
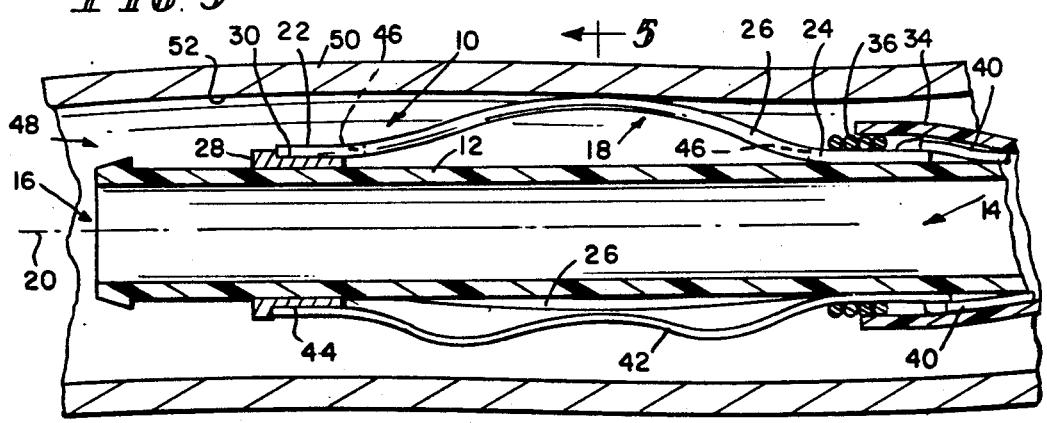
FIG. 4 is a view similar to that of FIG. 3 showing the two memory elements in their expanded configurations and the resulting movement of the core member to a "centered" position within the body passageway.

Apparatus 10 also includes an elongated tubular member 34 shown in FIGS. 1, 3, and 4 and terminating on base portion 14 of core member 12. Wire 36 or the like is wrapped around core member 12 to hold the attachment portions 24 of the three memory elements 18 tightly in place on the core member 12 as shown best in FIGS. 3 and 4. It will be understood that wires 36 provide means for clamping the attachment portions 24 of memory elements 18 to core member 12 so that attachment portions 24 do not move relative to core member 12 as the memory elements 18 change shape when heated causing the distal attachment portions 22 to move relative to core member 12 as shown in FIG. 4.

Apparatus 10 further includes a power supply 38 for supplying electrical power to memory elements 18 by means of electrical wires 40, which wires 40 are attached to memory elements 18 at their proximal attachment portions 24. A ground wire 42 is also provided for electrically grounding the apparatus. Ground wire 42 is attached to power supply 38 and, as shown in FIG. 4, terminates in a groove 44 provided in slip collar 28.

Figure 2:
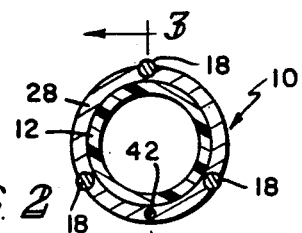
FIG. 2 is a transverse cross-sectional view taken along line 2—2 of FIG. 1 showing three memory elements uniformly spaced apart about the periphery of the core member.

In preferred embodiments, temperature-activated memory elements 18 are elongated strips formed of a mechanical memory metal such as a nickel titanium alloy. While such an alloy is preferable, other alloys having memory characteristics related to temperature can be used without departing from the scope of the invention. In general, such alloys have high resistances so that heat is produced when current is passed therethrough. The heating, in turn, raises the temperature of the alloy to a predetermined activation temperature. At this temperature, an elongated strip of the alloy will change shape by moving from an initial configuration to a predetermined, "memorized" configuration. As shown best in FIG. 2, apparatus 10 preferably includes three memory elements 18 spaced equiangularly about the circumference of core member 12.

Each memory element 18 of the illustrated apparatus is shown to include a shape memory portion 26 disposed between distal attachment portions 22 and proximal attachment portions 24. Barriers 46 are created in each memory element 18 to partition shape memory portion 26 from attachment portions 22, 24. Reference is hereby made to U.S. Pat. No. 4,777,799 to McCoy for a description of a technique for forming barriers such as barrier 46 in a memory element to preserve shape memory characteristics of shape memory portion 26. Essentially, while shape memory portion 26 and attachment portions 22, 24 comprise the normal crystalline internal structure of the alloy from which each memory element 18 is formed, barrier 46 comprises a thermally stressed dissimilar internal structure. The dissimilar internal structure is configured to block transmigration of selected ions between attachment portions 22, 24 and shape memory portion 26. The ion flow barrier aids in preventing significant ion contamination of each shape memory portion 26 by ions extant in attachment portions 22, 24.

The operation of positioning apparatus 10 is illustrated in FIGS. 3-4. Distal end 16 of apparatus 10 is inserted into a body passageway 48 defined by a blood vessel 50 or the like having an interior wall 52 as shown in FIG. 3. Initially, the memory elements 18 have a substantially straight shape as shown in FIGS. 1 and 3 causing the slip collar 28 to lie in an extended position. Thus, the shape memory portion 26 of memory element 18 lies adjacent to core member 12. This is advantageous in the case where passageway 48 is of a diameter only slightly larger than the diameter of core member 12.

Power supply 38 is operated to apply an electrical current to one or more of the memory elements 18. Because of the high resistance of memory elements 18, heat is generated. When a memory element 18 is heated to a predetermined transitional temperature, shape memory portion 26 of that memory element 18 moves away from its initial spot alongside the core member 12 to assume a predetermined shape. As shown in FIG. 4, the predetermined shape of memory element 18 is preferably one in which shape memory portion 26 is bowed away from core member 12 in engagement with interior wall 52.

Outward movement of shape memory portion 26 relative to core member 12 is possible because slip collar 18 is slidable along the longitudinal axis 20 of core member 12. As shape memory portion 26 moves outwardly toward interior wall 52, attachment portions 22 and slip collar 28 in which such portions are received slide relative to core member 12 from the extended positions shown in FIG. 3 to the retracted positions shown in FIG. 4.

Figure 5:
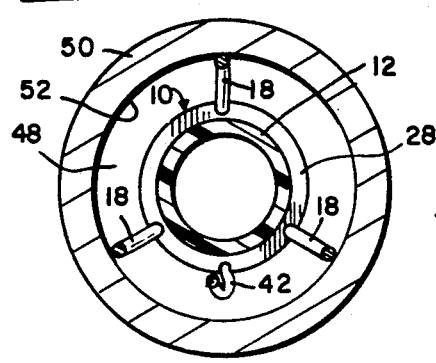
FIG. 5 is a transverse cross-sectional view taken along line 5—5 of FIG. 4 showing the orientation of all three memory elements in their expanded configuration about the periphery of a core member.

Advantageously, manipulation of the memory elements 18 enables an operator to achieve precise positioning of core member 12 in a predetermined orientation within passageway 48. For example, as shown in FIG. 5, memory elements 18 might be located equiangularly about the circumference of core member 12 and heated to move to assume predetermined shapes in engagement with interior wall 52 so as to align central longitudinal axis 20 of core member 12 with the central longitudinal axis of passageway 48.

Alternatively, a single memory element 18 might be heated, the single element being chosen, for example, to have a predetermined shape which would not be attained at the time when shape memory portion 26 came into engagement with interior wall 52. Rather, shape memory portion 26 would continue to attempt to move outwardly against wall 52, thereby biasing core member 12 in an opposite direction.

It is to be understood that the number of memory elements 18, their relative positions, and their particular predetermined shapes may all be varied in accordance with the precise positioning function sought to be achieved.

Also, it is to be recognized that control elements other than temperature-activated memory elements 18 may also be used as part of the claimed invention. For example, a spring or other resilient elongated metal strips could be substituted for memory elements 18. Since such substitutes would move in response to mechanical stimulus rather than an electrical current, power supply 38 and electrical wires 40 would be replaced by a mechanical control means. Such substitutions would not vary the function of apparatus 10 and could be made without departing from the scope of the invention.

When the desired manipulation is complete, the supply of electrical current to one or more of the memory elements 18 is cut off. Gradually the memory elements 18 cool and lose rigidity. In addition, the flexible walls of blood vessel 50, which may have been displaced slightly radially outwardly by the memory elements 18, move to resume their original position, thereby exerting a radially-inwardly directed force on memory elements 18. This restoring force supplied by the blood vessel 50, in addition to the increased flexibility of the memory elements 18 upon cooling, is sufficient to return memory elements 18 to an unexpanded configuration such as that shown in FIG. 3. The apparatus can then be moved further along the blood vessel for additional manipulation or can be readily withdrawn from the blood vessel altogether.

Another embodiment of the claimed invention is illustrated in FIGS. 6-10. In FIGS. 6-10, those elements referenced by numbers identical to those in FIGS. 1-5 perform the same of similar function. As shown in FIG. 6, a positioning apparatus 110 includes a core member 112 having a base portion 114 and a distal end 116.

Apparatus 110 preferably includes a pair of temperature-activated memory elements 18 extending parallel to longitudinal axis 120 of core member 112 and each having a distal attachment portion 22, a proximal attachment portion 24, and a shape memory portion 26 separated by a barrier 46 as previously described. As shown in FIG. 7, memory elements 18 are positioned about the circumference of core member 112 approximately at the "four o'clock" and "eight o'clock" positions, respectively, so that they bias core member 112 to an "off-center position" within a body passage as will be described below.

At distal end 116 of core member 112, apparatus 110 includes a slip collar 28 slidable relative to core member 112 and being formed to include grooves 30 for receiving distal attachment portions 22 of memory elements 18. A flange 32 formed at distal end 116 prevents slip collar 28 from disengaging core member 112 by sliding longitudinally beyond distal end 116.

Core member 112 is formed to include a longitudinally extending opening 122 allowing communication between a hollow interior chamber 124 formed in core member 112 and regions external to core member 112. A scraper 126 is provided in interior chamber 124 and is slidable therein relative to core member 112. Scraper 126 includes a longitudinally extending shaft 128 to which is appended a scraping blade 130 having a scraping face 132 directed toward distal end 116. Scraping blade 130 has a diameter essentially equal to the inner diameter of core member 112. Thus, scraping blade 130 projects outwardly from longitudinally extending opening 122 to communicate with regions adjacent to core member 112 so that any plaque or other material 142 lying in such regions can be scraped and then deposited into interior chamber 124. An end cap 134 is provided at distal end 116 of core member 112 to help retain the collected material 142 in interior chamber 124.

In operation, as shown in FIGS. 8-10, the apparatus 110 is inserted into a body passageway 136 defined by a blood vessel 138 or the like having an interior wall 140. Interior wall 140 has an accumulation 142 of plaque or the like deposited thereon. Advantageously, each memory element 18 initially lies in a position adjacent to core member 112 and slip collar 28 lies in an extended position as shown in FIG. 6.

Power is supplied to heat the memory element 18 in the manner heretofore described. As shown in FIG. 9, memory elements 18, when heated to their predetermined temperatures, will move to assume predetermined shapes 148 and move slip collar 28 to a retracted position on core member 112. The movement of memory elements 18 against interior wall 140 beyond the point of engagement with such wall 140 will bias core member 112 in a direction opposite to the radially outward direction of movement of memory element 18 so that the core member 112 is oriented in an off-center position out of alignment with a central longitudinal axis 152 of passageway 136 as shown, for example, in FIG. 9.

Such an off-center capability is desirable where the core member 112 can be urged by the memory elements 18 toward a portion of wall 140 containing plaque accumulation 142 as shown in FIG. 9. As is illustrated in FIGS. 9 and 10, longitudinally-extending opening 122 in core member 112 can be aligned with plaque accumulation 142 so that a portion of the plaque accumulation 142 extends into opening 122 when core member 112 is biased to an off-center position.

Next, shaft 128 is slid longitudinally relative to core member 112 thereby moving scraping blade 130 into engagement with plaque accumulation 142, at least to the extent to which plaque accumulation 142 extends through opening 122. As the shaft continues to slide, scraping blade 130 cleaves such portion of plaque accumulation 142. The cleaved material drops through opening 122 and slides across face 132 of scraping blade 130 to interior cavity 124 in core member 112. As scraper 126 is moved further, it continues to cleave new material while at the same time pushing the already-cleaved material into chamber 124 at distal end 116.

This procedure can be repeated until interior cavity 124 has been filled to its capacity with scraped material. Then, temperature-activated memory elements 18 are returned to their initial unbowed positions against the core member 112 and the catheter 110 is withdrawn from the body passageway and the material removed from cavity 124 for testing or disposal.

Figure 11:
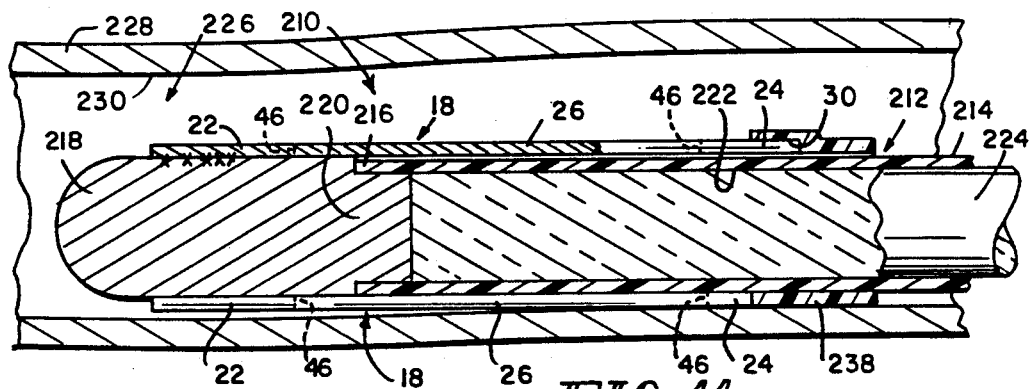
FIG. 11 is a fragmentary view of yet another embodiment of an apparatus in accordance with the present invention inserted into a body passageway using a sliding collar at the proximal end of the core member and showing temperature-activated memory elements in an initial configuration on the core member.
Figure 12:
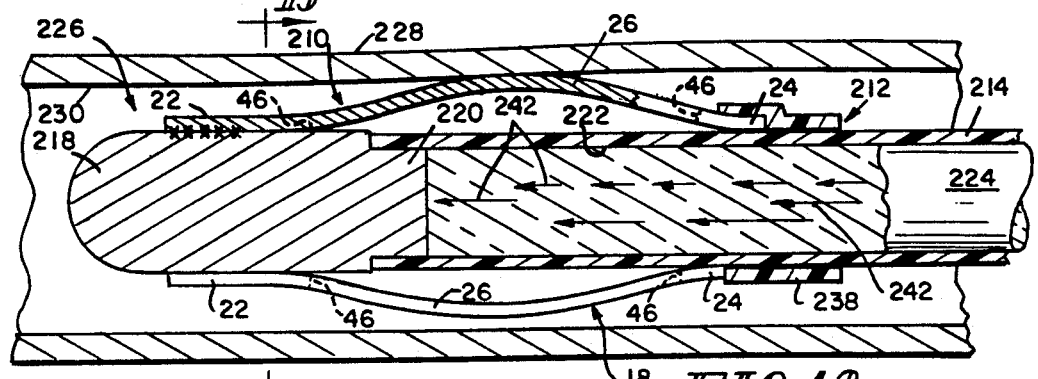
FIG. 12 is a view similar to FIG. 11 showing memory elements in an expanded configuration to center the core member in the body passageway.
Figure 15:
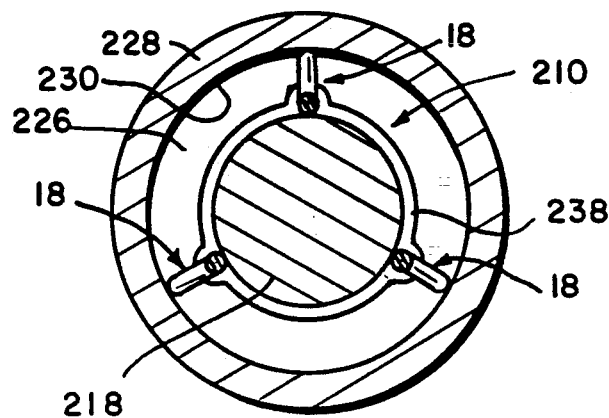
FIG. 15 is a transverse cross-sectional view taken along line 15—15 of FIG. 12 showing the orientation of memory elements in an expanded configuration about the periphery of a core member.

Another embodiment of the claimed invention is illustrated in FIGS. 11, 12, and 15. In FIGS. 11, 12, and 15, those elements referenced by numbers identical to those in FIGS. 1-10 perform the same or similar function. As shown in FIGS. 11, 12, and 15, an apparatus 210 has a core member 212 having base portion 214 and a distal end 216. Apparatus 210 also includes temperature-activated memory elements 18 formed in elongated strips and each including a distal attachment portion 22, a proximal attachment portion 24, and a shape member portion 26 separated by a barrier 46 as previously described. A slip collar 238 is provided to slidably couple each proximal attachment portion 24 to core member 212. Slip collar 238 is formed to include grooves 30 for receiving proximal attachment portions 24 so that such portions 24 slide longitudinally as slip collar 238 slides on core member 212.

Apparatus 210 is also provided with a distal cap 218 mounted at distal end 216 of core member 212. Distal cap 218 is formed of a heat-conductive material and includes a plug 220 extending into interior 222 of core member 212. Interior 222 of core member 212 also contains, illustratively, a fiber optic cable 224 or other means for directing energy from an energy source (not shown) to plug 220 of distal cap 218. Such energy source may illustratively be a laser for operating in conjunction with fiber optic cable 224.

Each distal attachment portion 22 is directly affixed to distal cap 218 so as not to slide relative to distal cap 218. The direct mounting of portions 22 onto distal cap 218 allows heat to be conducted between cap 218 and portions 22, and then to memory elements 18, heating memory elements 18 to cause memory elements 18 to move to assume a predetermined shape.

Fiber optic cable 224 is connected at its proximal end to an energy source (not shown) and at its distal end to plug 220. Thus, energy 242 from the energy source can be delivered by means of fiber optic cable 224 to heat plug 220 of distal cap 218 and memory elements 18. As shown in FIG. 15, apparatus 210 may include a plurality of memory elements 18 positioned about the circumference of core member 212 such that movement of shape memory portions 26 into engagement with interior wall 230 will position apparatus 210 as has been heretofore described.

A slip collar 238 is provided for sliding on core member 212 to move the proximal attachment portions 24 of memory elements 18 toward and away from the fixed distal cap 218. Whereas the slip collar 28 in the embodiments of FIGS. 1-18 was positioned near the tip of the core member and connected to the distal attachment portions 22, this slip collar 238 is positioned to slide on an inner portion 214 of core member 212 and connected to the proximal attachment portions 24. Otherwise, slip collar 238 behaves in a manner similar to slip collar 28 because it moves relative to core member 212 in response to movement of one or more of memory elements 18 under heat to assume a predetermined shape.

In operation, apparatus 210 is inserted into a body passageway 226 defined by a blood vessel 228 having an interior wall 230. Advantageously, memory elements 18 are in an initial straight position and slip collar 238 is in an initial extended position as has been described with respect to other embodiments of the invention.

Preferably, a laser beam 242 from the energy source (not shown) is directed at plug 220 of distal cap 218 via fiber optic cable 224. The laser beam 242 heats plug 220, and the heat is conducted throughout distal cap 218 to heat cap 218 to a predetermined temperature. From cap 218, the heat is conducted to each distal attachment portion 22 since distal attachment portions 22 are rigidly appended directly to cap 218. The heat is then, of course, distributed from each attachment portion 22 throughout each temperature-activated memory element 18. When memory elements 18 attain the predetermined temperature, shape memory portions 26 will move to assume a predetermined shape as shown in FIG. 12, thereby moving slip collar 238 to a retracted position closer to distal cap 218 as shown in FIG. 12.

Figure 13:
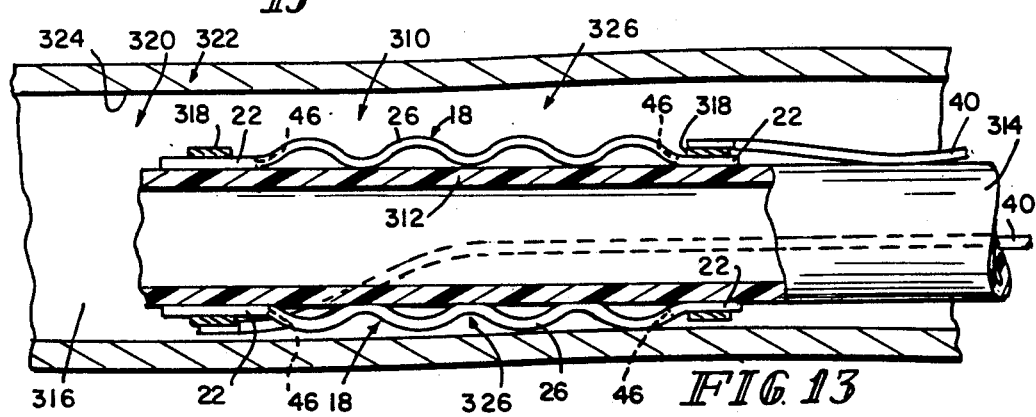
FIG. 13 is a fragmentary view of still another embodiment of an apparatus in accordance with the present invention inserted into a body passageway showing temperature-activated memory elements in an initial configuration on the core member, each memory element being fixed at its opposite ends rigidly to the core member.
Figure 14:
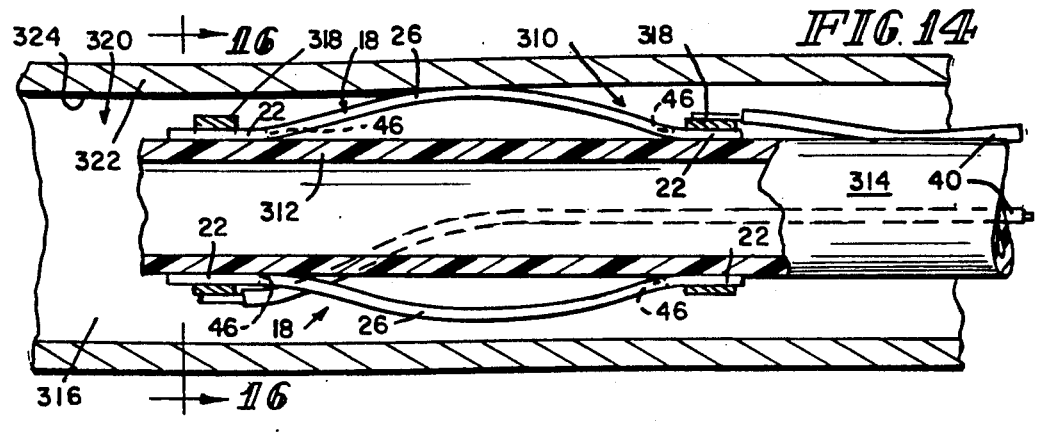
FIG. 14 is a view similar to FIG. 13 showing the memory elements in an expanded, predetermined configuration upon being heated by remote control.
Figure 16:
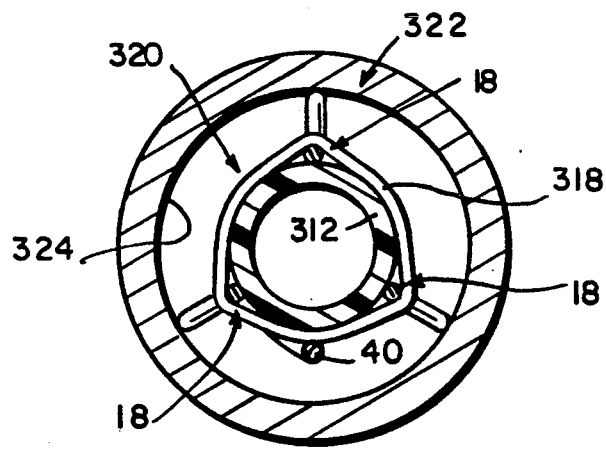
FIG. 16 is a transverse cross-sectional view taken along line 16—16 of FIG. 14 showing the orientation of memory elements in an expanded configuration about the periphery of a core member.

Another embodiment of the invention is illustrated in FIGS. 13, 14, and 16. In FIGS. 13, 14, and 16, those elements referenced by numbers identical to those in FIGS. 1-12 perform the same or similar function. As shown in FIG. 13, an apparatus 310 includes a core member 312 having a base portion 314 and a distal end 316 preferably includes temperature-activated memory elements 18. Each memory element 18 includes a distal attachment portion 22, a proximal attachment portion 24, and a shape member portion 26 each separated by a barrier 46 as previously described. As shown in FIG. 13, distal attachment portions 22 and proximal attachment portions 24 are rigidly affixed to core member 312 by non-slidable collars 318 or other attachment means. Lead wires 40 from a power supply (not shown) are also attached to collars 318 so as to conduct electrical current to collars 318 and thereby to temperature-activated memory elements 18. In FIG. 16, apparatus 310 is shown to include a plurality of temperature-activated memory elements 18 spaced equiangularly about the circumference of core member 312.

In operation, apparatus 310 is inserted into a body passageway 320 defined by a blood vessel 322 or the like having an internal wall 324. As shown in FIG. 13, memory elements 18 are initially in an undetermined configuration 326. It is to be understood that a serpentine configuration 326 is shown for illustrative purposes only. Another particular configuration may be chosen to suit specific design criteria.

Next, electrical current is supplied via leads 40 to heat one or more of memory elements 18 to a predetermined temperature at which shape memory portion 26 moves from the serpentine shape to assume a predetermined shape that is bowed as shown in FIG. 14.

In the illustrated embodiment, an excess length of memory material is provided to accommodate the movement of shape memory portion 26 to its predetermined shape as shown in FIG. 14. Thus, memory elements 18, upon being heated to the predetermined temperature, unfold to the predetermined shape. As has been previously described, memory elements 18 are configured so that when their shape memory portions 26 expand to assume their predetermined shape, such portions engage the interior wall 324 of body passageway 320 and thereby bias core member 312 to a particular position therein.

Although the invention has been described in detail with reference to the illustrated preferred embodiments, variations and modifications exist within the scope and spirit of the invention as defined in the following claims.

What is claimed is:

1. An apparatus for positioning a hollow core member relative to a central longitudinal axis of a passageway defined in a body by an internal wall of the body, the apparatus comprising at least two separate positioning elements, each positioning element including a pair of end portions and a flexible central portion appended to the end portions, the end portions being coupled to the hollow core member to arrange the two separate positioning elements in spaced-apart relation around the hollow core member, and control means coupled to the end portions of the two separate positioning elements for moving the central portions of each positioning element relative to the hollow core member to engage the internal wall defining the passageway without moving the attachment portions relative to the hollow core member so that the positioning elements move to position the hollow core member in a selected orientation within the passageway.

2. The apparatus of claim 1, wherein each positioning element comprises a shape memory alloy moving to assume a predetermined shape when heated to a predetermined temperature.

3. The apparatus of claim 2, wherein the control means includes means for selectively heating each positioning element to the predetermined temperature.

4. The apparatus of claim 2, wherein the passageway has a central longitudinal axis, and a plurality of separate positioning elements are spaced about the circumference of the hollow core member, the central portions of each of the positioning elements moving in an outward direction away from the hollow core member to assume a predetermined shape when heated to a predetermined temperature, the central portions of the positioning elements acting against the interior wall to center the hollow core member within the passageway along the central longitudinal axis.

5. The apparatus of claim 1, wherein the positioning elements are spaced equiangularly about the circumference of the hollow core member.

6. The apparatus of claim 1, wherein the hollow core member includes an exterior surface and the central portion lies adjacent the exterior surface and is movable relative to the exterior surface.

7. An apparatus for positioning a hollow core member within a passageway formed in a body, the apparatus comprising means for moving the hollow core member to a selected orientation within the passageway and relative to an internal wall defining the passageway, the moving means including at least two temperature-activated memory elements, each temperature-activated memory element having spaced-apart end portions coupled to the hollow core member and a central portion disposed intermediate the end portions and configured to move with respect to the hollow core member when heated to a predetermined temperature, and control means for selectively heating each memory element to the predetermined temperature to move the central portion away from the hollow core member to engage the internal wall of the passageway, thereby positioning the hollow core member in the selected orientation within the passageway, the control means being coupled to the end portions of each memory element.

8. The apparatus of claim 7, further comprising collar means for slidably coupling one of the end portions of each memory element to the hollow core member.

9. The apparatus of claim 8, wherein the hollow core member includes proximal and distal portions, a first of the end portions of each memory element is rigidly connected to the proximal portion of the hollow core member, and a second of the end portions of each memory element is slidably connected to the distal portion of the hollow core member by the collar means.

10. The apparatus of claim 9, wherein the control means includes a power supply and lead wires interconnecting each of the end portions in electrical communication and the power supply.

11. The apparatus of claim 10, wherein the hollow core member includes an exterior surface and the lead wires extend along the hollow core member adjacent to the exterior surface.

12. The apparatus of claim 10, wherein the core member includes an exterior wall and the lead wires are embedded in the exterior wall.

13. The apparatus of claim 8, wherein the hollow core member includes proximal and distal ends, a first of the end portions of each memory element is fixed to the proximal portion of the hollow core member at a junction point, the collar means is mounted on the hollow core member and slidable between the distal end and the junction point, and a second of the end portions of each memory element is coupled to the collar means for sliding movement therewith.

14. The apparatus of claim 13, wherein the hollow core member has a longitudinal axis, the central portion of each memory element moves in a radially outwardly extending direction away from the longitudinal axis of the hollow core member upon being heated to its predetermined temperature to slide the collar means along the hollow core member in a direction toward the junction point of the first end portion and the proximal portion of the hollow core member.

15. The apparatus of claim 7, wherein the passageway has a central longitudinal axis, the moving means includes a plurality of separate temperature-activated memory elements spaced about the circumference of the hollow core member so that the memory elements, when heated to assume a predetermined shape, center the hollow core member about the central longitudinal axis of the passageway.

16. The apparatus of claim 15, wherein the plurality of temperature-activated memory elements is spaced equiangularly about the circumference of the hollow core member.

17. The apparatus of claim 7, wherein the hollow core member includes an exterior surface and the central portion is movable between a first position adjacent the exterior surface and a second position away from the exterior surface in response to being heated to its predetermined temperature.

18. An apparatus for positioning a core member within a passageway formed in a body, the apparatus comprising means for moving the core member within the passageway relative to an internal wall defining the passageway, the moving means including at least one temperature-activated memory element having spaced-apart attachment portions coupled to the core member and a shape memory portion disposed intermediate the attachment portions and configured to move with respect to the core member when heated to a predetermined temperature, and control means for selectively heating the at least one memory element to the predetermined temperature to move the shape memory portion away from the core member to engage the internal wall of the passageway, thereby positioning the core member in a selected orientation within the passageway, the control means being coupled to the attachment portions of the at least one memory element, and collar means for slidably coupling one of the attachment portions to the core member, the core member including proximal and distal portions, a first of the attachment portion being rigidly connected to the proximal portion of the core member, and a second of the attachment portions being slidably connected to the distal portion of the core member by the collar means, the control means including a power supply and lead wires interconnecting each of the attachment portions in electrical communication and the power supply, the collar member being formed of an electrically conductive material, and further comprising a lead wire interconnecting the collar and the core member to provide an electrical ground.

19. An apparatus for positioning a core member or the like within a passageway formed in a body, the apparatus comprising means for moving the core member toward an internal wall defining the passageway and away from a center axis of the passageway to an off center position within the passageway, the moving means including a plurality of axially extending temperature-activated memory elements coupled to the core member and arranged in circumferentially spaced-apart relation around the core member, and means for selectively heating the temperature-activated memory elements to predetermined temperatures to alter the shape of the temperature-activated memory elements so that portions thereof engage the internal wall to move the core member to said off center position as the shape of the temperature-activated memory elements undergoes alteration.

20. The apparatus of claim 19, wherein each memory element has a pair of end portions, and a flexible central portion appended to the end portions, and further including collar means for slidably coupling an end portion to the core member.

21. The apparatus of claim 19, wherein the core member has a proximal end coupled to a base and terminates in a distal end, and each memory element has a pair of end portions and a flexible central portion appended to the end portions, and further including collar means for slidably coupling an end portion to the distal end of the core member.

22. An apparatus for positioning a hollow core member within a passageway formed in a body, the hollow core member being formed to include a lumen and having a proximal end coupled to a base and terminating at a distal portion, the distal portion being formed to include an opening into the lumen formed in the hollow core member, the apparatus comprising at least one control element having a pair of end portions and a flexible central portion appended to the end portions, means for anchoring a first of the end portions to the proximal end of the hollow core member at a junction point, collar means for slidably coupling a second of the end portions to the distal portion of the hollow core member to permit movement of the flexible central portion relative to the hollow core member in response to sliding movement of the second end portion between the distal portion and the junction point, and control means for moving the central portion relative to the hollow core member to engage an interior wall lying in the body and defining the passageway to control the position of the lumen opening formed in the distal portion of the core member in the passageway.

23. The apparatus of claim 22, wherein the hollow core member has a longitudinal axis, the central portion moves in an outward direction away from the longitudinal axis of the hollow core member to slide the collar means along the hollow core member in a direction toward the junction point of the first end portion and the proximal end of the hollow core member.

24. The apparatus of claim 22, wherein the at least one central element comprises a shape memory alloy.

25. The apparatus of claim 24, wherein the passageway has a central longitudinal axis, and a plurality of control elements are spaced about the circumference of the hollow core member, the central portions of each of the control elements moving in an outward direction away from the hollow core member to assume a predetermined shape when heated to a predetermined temperature, the central portions of the control elements acting against the interior wall during movement in said outward direction to center the lumen opening formed in the distal portion of the hollow core member along the central longitudinal axis within the passageway.

26. The apparatus of claim 25, wherein the plurality of control elements is spaced equiangularly about the circumference of the core member.

27. The apparatus of claim 22, wherein the distal portion of the core member includes an end face and an axially extending side wall and the end face is formed to include the opening into the lumen.

28. An apparatus for positioning a core member within a passageway formed in a body, the core member having a proximal end coupled to a base and terminating at a distal end, the apparatus comprising at least one control element having a pair of end portions and a flexible central portion appended to the end portions, means for anchoring a first of the end portions to the proximal end of the core member at a junction point, collar means for slidably coupling a second of the end portions to the distal end of the core member to permit movement of the flexible central portion relative to the core member in response to sliding movement of the second end portion between the distal end and the junction point, and control means for moving the central portion relative to the core member to engage an interior wall lying in the body and defining the passageway to control the position of the core member in the passageway, the at least one control element comprising a shape memory alloy, the collar means being formed of an electrically conductive material, and further comprising a lead wire interconnecting the collar means and the core member to provide an electrical ground.

29. An apparatus for positioning a hollow core member relative to a central longitudinal axis of a passageway defined in a body by an internal wall of the body, the apparatus comprising a plurality of separate elongated temperature-activated memory elements aligned in spaced-apart parallel relation to one another, each elongated memory element including a pair of end portions coupled to the hollow core member and a flexible central portion extending between the end portions, and control means for heating the elongated temperature-activated memory elements to move at least the central portions thereof relative to the hollow core member and against the internal wall defining a passageway so that the hollow core member moves to a selected orientation within the passageway.

30. The apparatus of claim 29, wherein the control means includes means for selectively heating all of the memory elements to center the hollow core member within the passageway along the central longitudinal axis.

31. An apparatus for positioning a catheter relative to a central longitudinal axis of a passageway defined in a body by an internal wall of the body, the apparatus comprising a plurality of separate elongated temperature-activated memory elements aligned in spaced-apart parallel relation to one another, each elongated memory element including a pair of end portions coupled to the catheter and a flexible central portion extending between the end portions, and control means for heating the elongated temperature-activated memory elements to move at least the central portions thereof relative to the catheter and against the internal wall defining a passageway so that the catheter moves to a selected orientation within the passageway, the control means including means for selectively heating certain ones of the memory elements to move the catheter away from the central longitudinal axis to an off-center position within the passageway.

* * * * *